United States Patent
Filsoof (10) Patent No.: US 11,351,053 B2
(45) Date of Patent: Jun. 7, 2022

(54) NECK SUPPORT DEVICE

(71) Applicant: Mahmud Filsoof, Pacific Palasade, CA (US)

(72) Inventor: Mahmud Filsoof, Pacific Palasade, CA (US)

( * ) Notice: Subject to any disclaimer, the term of this patent is extended or adjusted under 35 U.S.C. 154(b) by 0 days.

(21) Appl. No.: 16/558,133

(22) Filed: Sep. 1, 2019

(65) Prior Publication Data

US 2020/0390582 A1  Dec. 17, 2020

Related U.S. Application Data (60) Provisional application No. 62/862,018, filed on Jun. 15, 2019.

(51) Int. Cl.
  *A61F 5/05* (2006.01)
  *A61F 5/055* (2006.01)
  *A61F 5/058* (2006.01)

(52) U.S. Cl.
  CPC .......... *A61F 5/055* (2013.01); *A61F 5/05883* (2013.01)

(58) Field of Classification Search
  CPC .. A61F 5/01; A61F 5/0102; A61F 5/02; A61F 5/022; A61F 5/024; A61F 5/026; A61F 5/028; A61F 5/04; A61F 5/042; A61F 5/048; A61F 5/05; A61F 5/055; A61F 5/0508; A61F 5/05883; A61F 5/37; A61F 5/3707; A61F 2005/0197; A61F 2005/0179; A61F 5/058; A61H 1/0218; A61H 1/0229; A61H 1/0292; A61H 1/0296
  USPC ... 602/32, 33, 34, 35, 36, 37, 38, 39, 40, 18
  See application file for complete search history.

(56) References Cited

U.S. PATENT DOCUMENTS

| | | | | |
|---|---|---|---|---|
| 2,474,690 A | * | 6/1949 | Robinson | B08B 9/0436 403/229 |
| 2,820,455 A | * | 1/1958 | Hall | A61F 5/055 602/18 |
| 3,177,869 A | * | 4/1965 | Bartels | A61F 5/055 602/18 |

(Continued)

*Primary Examiner* — Kim M Lewis
(74) *Attorney, Agent, or Firm* — Alexander Chen, Esq.

(57) ABSTRACT

A head and/or neck support device that comprises an extended-half-round shape, soft base; a belt that is attached to the base; a vertical angled bracket that comprises a protruding upward hollow cylinder, and is attached to the base; a first cylinder whose near end is disposed within the angled bracket, and whose far end is male threaded; a radial ring that is attached to the outer side of the first cylinder near the far end thereof; a hollow second cylinder whose near end is female threaded, and far end has a ring attached. The far end of the first cylinder is screwed into the second cylinder's near end. The devise further comprises a chin support component that comprises a hollow third cylinder, a chin rest component, and an end cap. The far end of the second cylinder is disposed within the third cylinder. The device further comprises a spring that is disposed within the third cylinder, and sandwiched between the cavity of the third cylinder and the second cylinder's far end. The device further comprises a chain that threads through the center of the spring, and whose near end is attached to the ring on the end of the second cylinder, and whose far end is attached to the cavity of the end cap. The opening at the far end of the third cylinder has a smaller diameter than the spring.

8 Claims, 6 Drawing Sheets

(56) References Cited

U.S. PATENT DOCUMENTS

| | | | |
|---|---|---|---|
| 3,601,123 A | | 8/1971 | McFarland |
| 3,795,243 A | * | 3/1974 | Miller .................... A61F 5/055 602/36 |
| 4,955,368 A | | 9/1990 | Heimann |
| 5,195,947 A | * | 3/1993 | Bode ...................... A61F 5/055 602/17 |
| 9,717,530 B1 | * | 8/2017 | Ross ................. A61B 17/6491 |
| 9,949,758 B2 | * | 4/2018 | Vikinsky ............ A61B 17/6458 |
| 2009/0198163 A1 | * | 8/2009 | Senyei .................... A61F 5/048 602/17 |
| 2010/0087764 A1 | * | 4/2010 | Linares .................. A61F 5/055 602/18 |
| 2015/0245940 A1 | * | 9/2015 | Hardcastle ......... A63B 21/4025 602/18 |
| 2018/0228515 A1 | * | 8/2018 | Ross ..................... A61B 17/66 |

* cited by examiner

NECK SUPPORT DEVICE

FIELD OF INVENTION

The present invention is directed generally to a system and apparatus for neck therapy that addresses the need for ventilation. Specifically, it is directed to a system and apparatus of a neck support for medical purposes that reduces the potential for moisture accumulation on the user's skin as compared to traditional neck support apparatuses.

BACKGROUND OF THE INVENTION

Neck braces or cervical collars are commonly used within the medical and therapeutic communities to support a patient's neck whose muscle, cervical vertebrae, or discs have received trauma. Because of the critical nerves involved in the neck, and the fact that an adult's head generally weighs around 10 lbs which is entirely supported by the neck when the neck is weakened, it is important to support and stabilize the mass of the patient's head in order to avoid further injuries and complications. The braces and collars generally immobilize the wearer's head while relieving the pressure on the spine by structurally supporting the weight of the head against the patient's upper chest, shoulders, and clavicle region.

The purpose of a collar is to support the spinal column and supporting structures such as the ligaments and muscles from loads and stresses that can cause pain and movement of the neck bones. It also maintains the bone alignment and limits the movement in your neck whilst the bones and ligaments heal There are many neck braces, or, in general, neck support devices, in the market. Most of them is made of foam and bulky. They wrap around, and completely surround the user's neck. These neck braces are difficult to ventilate, wearing a brace will increase your body temperature in that region, causing moisture to accumulate, and, as a consequence, the user's neck becomes sweaty and irritated from the accumulated sweat. While sometimes it may simply be a matter of adjusting or refitting the collar.

This discomfort is exacerbated during summer months or in tropical or warmer climates. This discomfort potentially may interfere with the neck therapy the user is receiving. Ultimately, the fault of these neck braces is that they rest the weight of the user's head, neck and the braces on the base of the neck and/or the shoulders. Thus, they wrap around a user's neck and must be somewhat rigid and solid. Thus, most of the current neck braces on the market don't ventilate very well.

Because the brace is itchy, uncomfortable and sweaty conditions, many users don't use them according to the directions given to them by their healthcare providers, removing them when they shouldn't, or poke and prod around the braces attempting to relieve discomfort.

Obviously, this is counterproductive and may by itself cause health problems or at minimum, exacerbate the patient's original injuries that the neck brace is meant to treat.

What is frustrating however is that as to the current state of the art, when a patient perseveres this discomfort and does use the neck brace according to a healthcare providers direction it is known that the cervical collars seen in the marketplace can cause pressure sores or ulcers.

Pressure injuries can be difficult to treat and can lead to serious complications. Pressure sores (more recently called pressure injuries) are areas of damage to the skin and underlying tissue caused by constant pressure or friction. By wearing a collar, a patient increases the local skin temperature between the device and their skin, thus naturally causing skin perspiration in and around the area. This moisture can exasperate the issue and cause skin breakdown.

Pressure sores are graded to four levels, including:

grade I—skin discolouration, usually red, blue, purple or black This is the mildest stage. These pressure sores only affect the upper layer of your skin.

Symptoms: Pain, burning, or itching are common symptoms. The spot may also feel different from the surrounding skin: firmer or softer, warmer or cooler.

grade II—some skin loss or damage involving the topmost skin layers. This happens when the sore digs deeper below the surface of your skin.

Symptoms: The skin is broken, leaves an open wound, or looks like a pus-filled blister. The area is swollen, warm, and/or red. The sore may ooze clear fluid or pus. And it's painful.

grade III—necrosis (death) or damage to the skin patch, limited to the skin layers.

grade IV—necrosis (death) or damage to the skin patch and underlying structures, such as tendon, joint or bone.

Both simple grade 1 pressure ulcers (redness, intact skin) and grade 2 ulcers (partial thickness loss of skin, shallow open blister) can be self-managed by applying a skin protector or dressing. Further grades of pressure ulcers require contacting the neurosurgical team as more complicated intervention is required.

In patients with moist skin, skin breakdown is increased fourfold, compared to those with dry skin.

Also, when a patient doesn't clean their brace regularly, they not only start to smell bad, but they also can sometimes cause health problems, such as folliculitis, ringworm and even staph infections.

To alleviate and prevent these issues, healthcare providers recommended that a patient take the following precautions: (1) Keep the skin clean, dry and cool; (2) Maintain hygiene under the collar, cleaning the skin under the collar daily; washing with warm soapy water and drying thoroughly; and (3) Changing pads on the neck brace/collar if they become wet.

While these recommendations seem fairly innocuous, as discussed, neck injuries are particularly serious and the potential for needless risk must be considered.

Accordingly, it is desirable to have a neck brace or neck support device that provides adequate support to the neck while allowing air circulation and ventilation, such that a user or patient is not required to remove the brace in order to dry and clean the neck and brace.

Further, as discussed, the current state of the art devices most often wrap around a user's neck and are rigid and solid in nature. Because of this, the devices are most often made by injection molding solid plastic pieces. As a consequence, and in order to bring down production costs, the devices currently seen in the market, are fairly limited when it comes to sizes and adjusting the fit of these devices.

Most commonly, current devices are manufactured in a gross range of small, medium, and large size variability, with the ability to tighten and somewhat customize the snugness limited to the number of adjustment points that can be molded into the plastic, similar to the size adjustment that one might expect with a snapback baseball cap, or ski bindings, and the like. Alternatively, with the foam variants of neck braces, in lieu of a rigid adjustment lock-in point, those devices often employ Velcro. While Velcro does allow for a more custom fit, anyone familiar with Velcro will readily recall that it often loses its grip such that a tight fit is difficult to maintain. Additionally, the foam used in these braces, much like with foam mattresses, retain heat, and exasperate the above describes moisture issues.

As such, it is additionally desirable to have a neck brace or neck support device that provides adequate support to the neck while allowing for customization of fitting on a micro incremental scale, a better fit granting better overall comfort, and likely leading to better healing and a higher quality of life for a user when using the device for prolonged periods as are often required with such injuries.

SUMMARY OF THE INVENTION

A head and/or neck support device that comprises an extended-half-round shape, soft base; a belt that is attached to the base; a vertical angled bracket that comprises a protruding upward hollow cylinder, and is attached to the base; a first cylinder whose near end is disposed within the angled bracket, and whose far end is male threaded; a radial ring that is attached to the outer side of the first cylinder near the far end thereof; a hollow second cylinder whose near end is female threaded, and far end has a ring attached. The far end of the first cylinder is screwed into the second cylinder's near end. The devise further comprises a chin support component that comprises a hollow third cylinder, a chin rest component, and an end cap. The far end of the second cylinder is disposed within the third cylinder. The device further comprises a spring that is disposed within the third cylinder, and sandwiched between the cavity of the third cylinder and the second cylinder's far end. The device further comprises a chain that threads through the center of the spring, and whose near end is attached to the ring on the end of the second cylinder, and whose far end is attached to the cavity of the end cap. The opening at the far end of the third cylinder has a smaller diameter than the spring.

In one embodiment, turning the radial ring extends or contracts the support device.

In another embodiment, the radial ring has a larger diameter than the second cylinder's.

In yet another embodiment, the end cap is female threaded.

In yet another embodiment, the third cylinder is male threaded.

In yet another embodiment, the third cylinder is crewed into the end cap.

In yet another embodiment, the chin rest component is molded to the outer side of the third cylinder.

In yet another embodiment, the chin rest component is attached to the outer side of the third cylinder.

DETAILED DESCRIPTION OF THE CURRENT INVENTION

Figure 1:
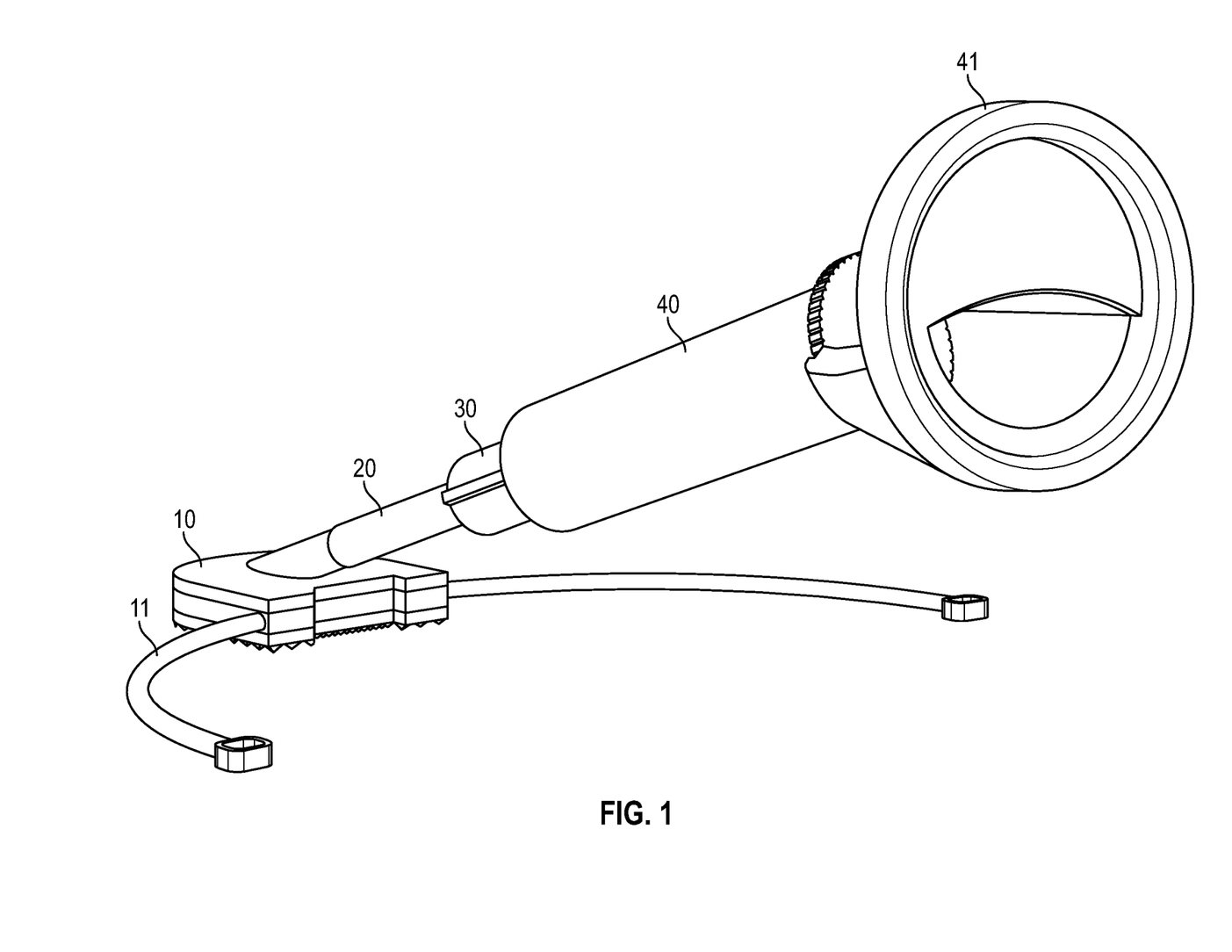
FIG. 1 illustrates a fully assembled embodiment of the current invention.

In FIG. 1, a fully assembled embodiment 1 of the current invention is depicted. This embodiment 1 comprises a base component 10 that, when in use, rests on the user/patient's sternum and supports the weight pushing down on the device. The base component 10 further comprises a belt 11 that is attached to the base and extends and wraps around the user/patient's body to the back, and its two ends hook on each other. The embodiment 1 further comprises a cylinder 20 that is inserted into the cylinder slot on the base 10. The cylinder 20 extends upward and screws into a cylinder 30. This cylinder 30 is, in turn, partially disposed inside the hollow cylinder of a component 40 that comprises the hollow cylinder and a chin rest 41 that is molded onto the outer side of the hollow cylinder.

Figure 2:
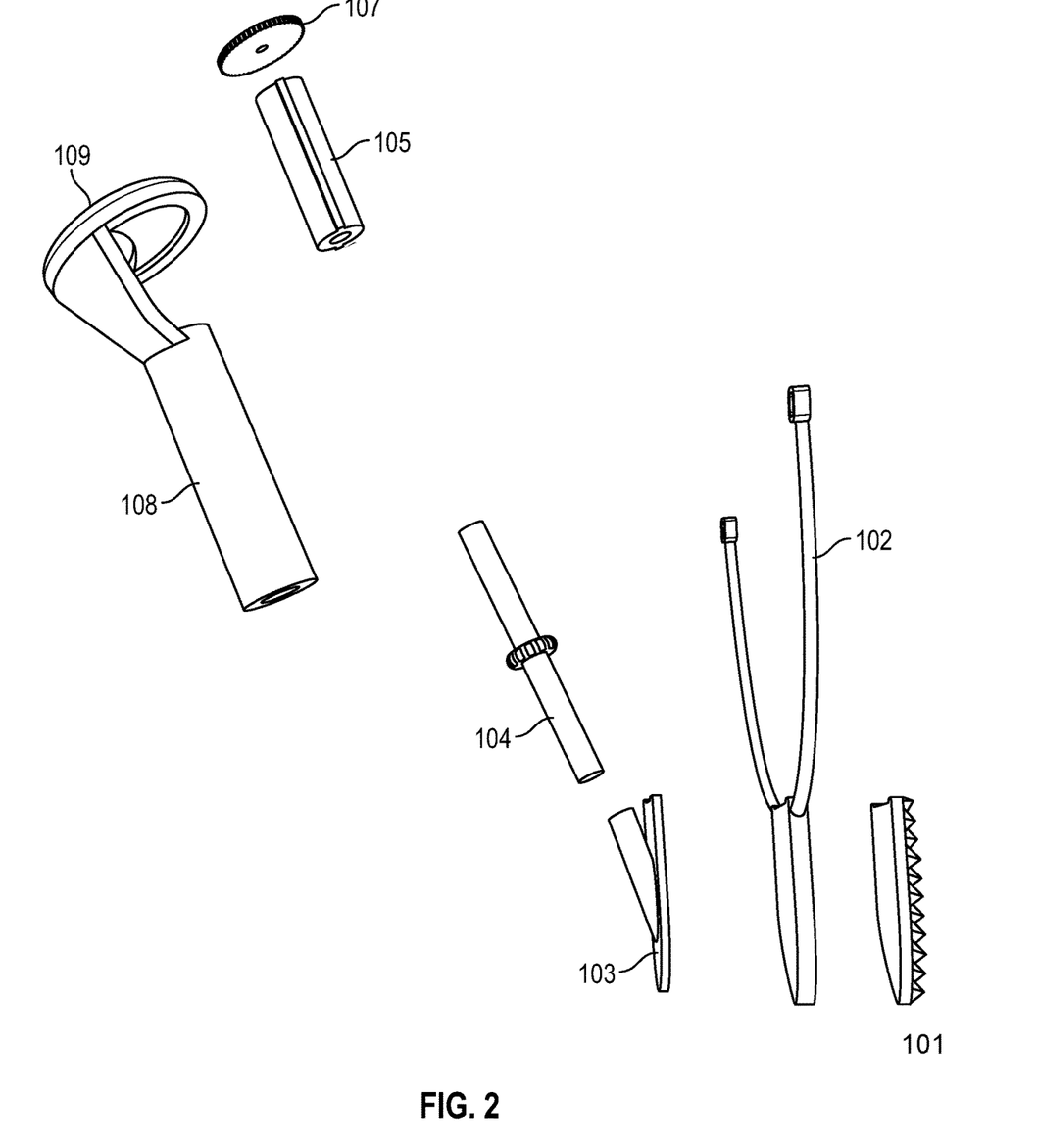
FIG. 2 is a pictorial illustration of an exploded view of the invention meant to communicate the various individually machine produced components, their approximate location to other components in the final assembly, and a suggestion of materials making up those components.

Reference is now made to FIG. 2, a pictorial illustration of an exploded view of the invention meant to communicate the various individually machine produced components, their approximate location to other components in the final assembly, and a suggestion of materials making up those components, constructed and operative in accordance with an embodiment of the present invention.

As with neck braces that are currently common, a majority of the components in the preferred embodiment of the invention at issue are either injected molded plastics and or some other combination of light weight cost effective metals and alloys in order to keep both the cost of the device itself practical, but balanced against the need for lightweight but sufficiently strong materials that can be expected to support the weight of the users head for the purposes of the device while keeping the cumulative weight of the device light and comfortable for the user such that it is easy to wear for the extended period of time that the invention is expected to be used.

In FIG. 2, an embodiment of the current invention in one part comprises three large horizontally bisected flattened capsule-shaped plates that stack to create the support base of the device, similar to the support base 10 disclosed supra in FIG. 1. Component 103 is a thick hard rubberized material piece that is designed with an incorporated angled subset cylinder which allows a cylindrical structure to be disposed within. Component 103 is, in turn, stacked on top of component 102, a similar bisected flattened capsule plate which will provide support for the device and which incorporates the two curved attachment arms which each have a mechanical attachment point at their ends. An adjustable belt will connect to these arms of 102 that will wrap and follow around the user's back to provide support for the device. Component 102 is, in turn, stacked on top of component 101, which is the innermost user facing layer of this 3 part support base and designed to have soft padding and to rest at the top of the user's sternum.

As was discussed previously, the design and mechanics of the current invention is the emphasis of this patent. As such, it is contemplated that many of the materials used for the components of the invention would be the same or similar as many of the same materials used in the current state of the art. As such, it is anticipated that injected molded plastic processes, aluminum, stainless steel, titanium, and other light weight, cost effective, medically appropriate materials will be sourced as to the current invention.

In FIG. 2, the embodiment of the current invention further comprises additional cylindrical components which comprise the mechanical support arm apparatus for the user's chin, neck and head. Cylinder 104 is disposed within the subset cylinder cavity of component 103 to provide support for cylinders 105 and 108. Cylinder 105 is female threaded to receive cylinder 104, which is male threaded. Both cylinders 104 and 105 are threaded with fine threads such that the height or length of this support arm can be extended and refined in micro increments and allow for very flexible adjustment and thus provide a more precise support for the neck as compared to traditional neck braces currently seen in practice. The embodiment further comprises a cap 107 that is attached to the end of the cylinder 108 when the embodiment is fully assembled. Cylinder 108 extends up and further comprises an incorporated soft chin support component 109 upon which the users rests their chin.

The embodiment further comprises a spring (not shown in FIG. 2) that is disposed within Cylinder 108's cavity and sandwiched and compressed between cylinder 105 and cylinder 108's cavity. The spring elasticity allows for limited and controlled neck movement, and softens the prodding force against the chin similar to shock absorbers seen in the automotive industry. For example, while the neck is tilted at a 15 degree angle the spring will assist in relieving pressure.

Cylinder 108 further comprises a locking mechanism that allows cylinder 105 and the spring to lock at a user's desired angle, similar to the locking mechanisms seen in retractable ballpoint ink pens. While locking the spring creates a static and rigid support, more traumatic and complicated neck injuries often initially require little to no movement early on in the recovery period. Furthermore, many patients experience fatigue over the course of the day, and it is desirable to incorporate this locking functionality such that the device can be fitted and turned to suit the needs of the patient.

Figure 3:
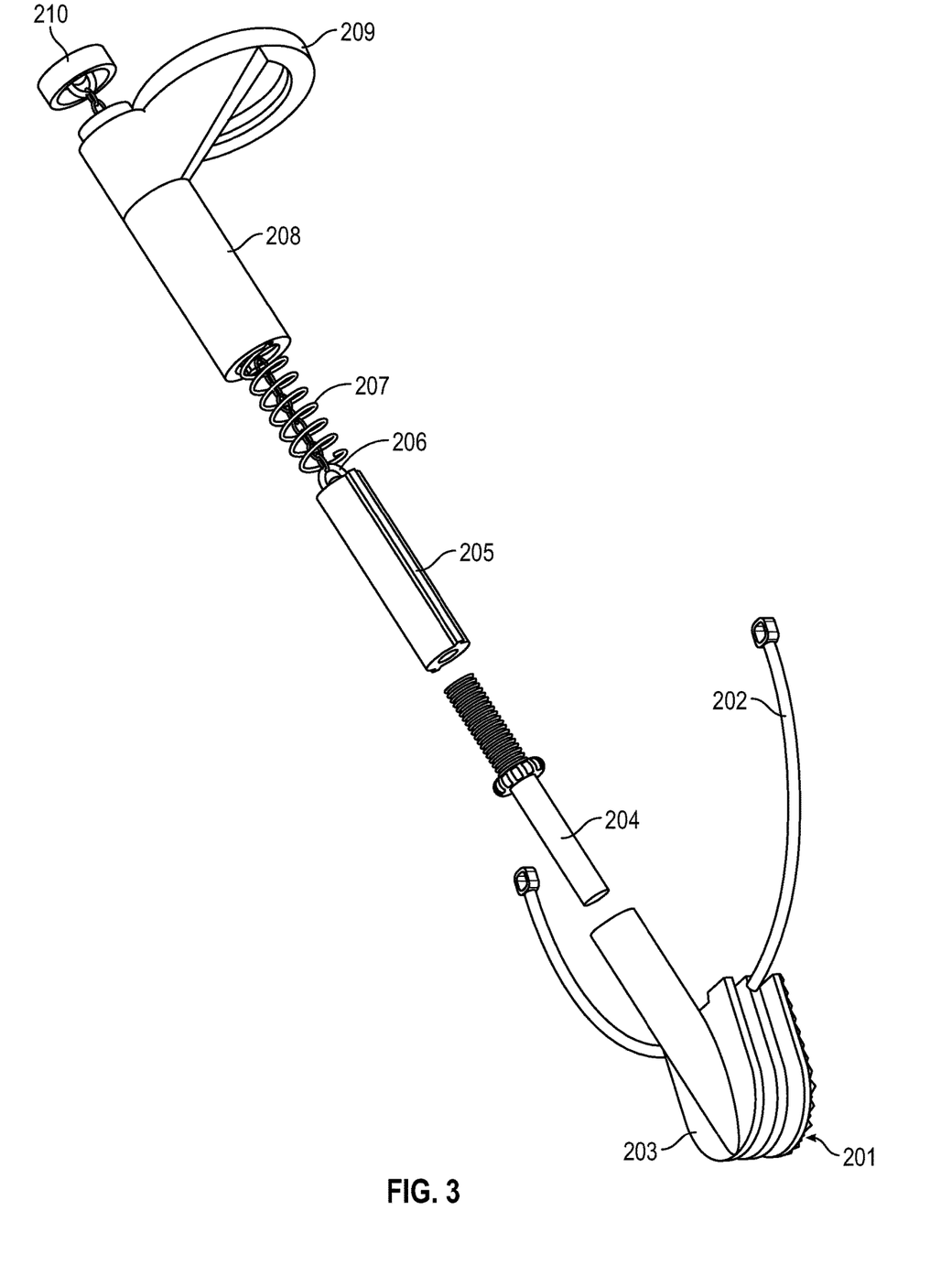
FIG. 3 is a pictorial illustration of an exploded side view of the invention, meant to communicate more specifically the assembly of the various individually machine produced components.
Figure 4:
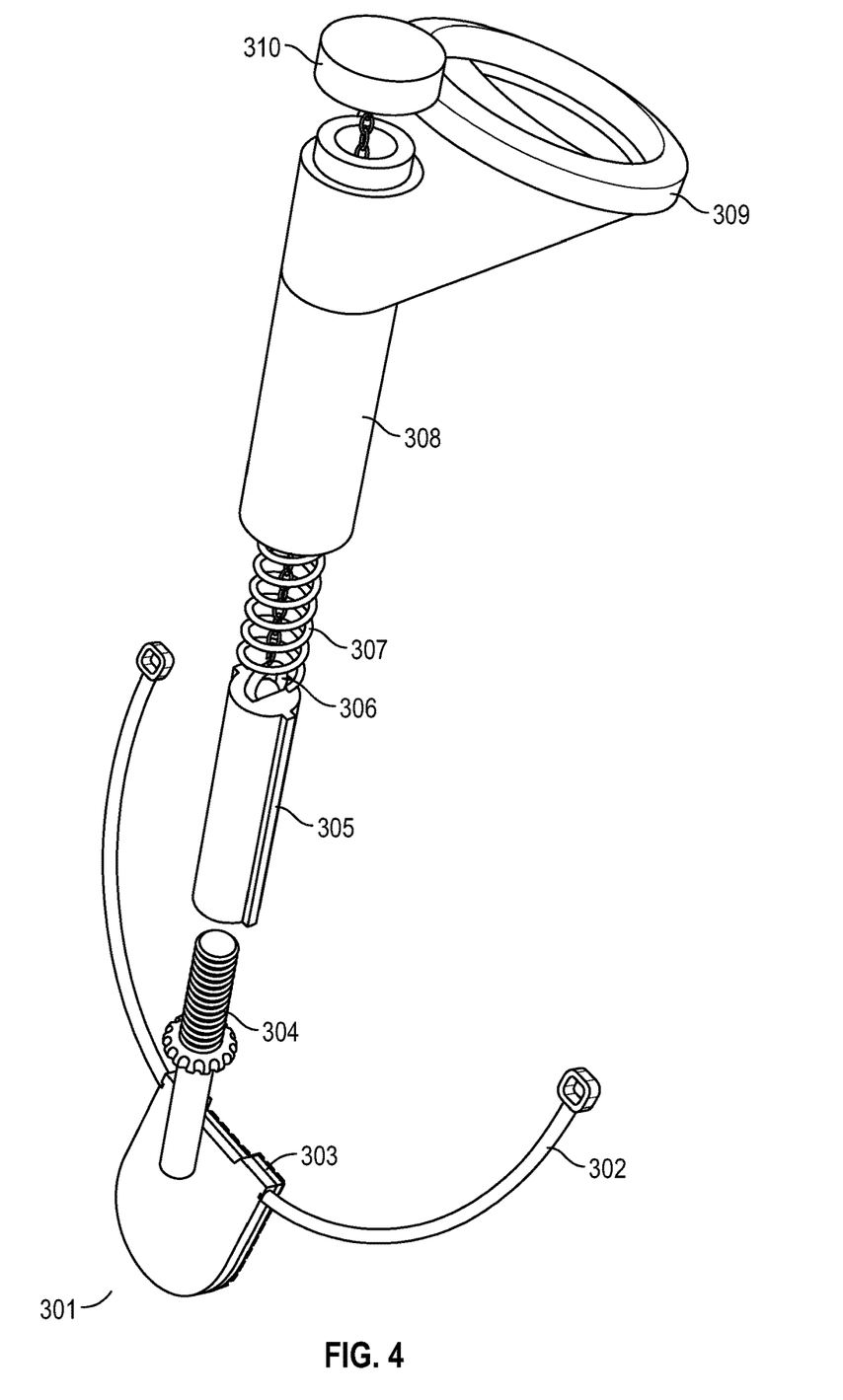
FIG. 4 is a pictorial illustration of an exploded view of the invention, similar to FIG. 2., but from a top-side favored perspective viewpoint.

Reference is now made to FIGS. 3 and 4 which are meant to communicate additional views of the device, with emphasis on the construction of the overall device and the relation between the various components.

FIG. 3 is a perspective and partially exploded view of an embodiment of the current invention, from a low angle, indicating the major components and how they attach, nest, or lock together. This embodiment comprises a user-facing base pad 201, middle-layer component of the base 202 where the curved attachment arms are attached and extend from, and bracket 203 that allows a cylindrical structure 204 to be disposed. The cylinder 204 further comprises a radial ring disposed about the midsection thereof. The far end of the cylinder 204 is male threaded, and screwed into the female threads of a hollow cylinder 205, that is female threaded to receive the threaded end of the cylinder 204. The cylinder 205 further comprises a hanging loop or ring 206 attached to the far end thereof. Through the hanging loop 206, a chain is disposed. The other end of the chain is disposed through a hanging loop or ring attached to the bottom of a cap 210. The embodiment further comprises a spring 207 that is disposed in a hollow cylinder 208's cavity. The chain is disposed through the center of the loops of the spring 207. The cylinder 208 further comprise a chin rest 209.

FIG. 4 is another perspective and partially exploded view of an embodiment of the current invention from a high angle. Notably, both FIG. 3 and FIG. 4 do not depict all components of the device and leave out the chain which locks and compresses the spring. Additionally, neither FIG. 3 nor FIG. 4 indicates the approximate location and scale of the threading on the cylinders which enables the fine adjustment of the height of the support arm. The embodiment depicted in FIG. 4 comprises a bracket base 301 where attachment arms 302 are attached and extend from. The embodiment further comprises a cylinder 304 that is disposed within a hollow cylinder that is attached to a bracket (which was described supra) that is attached to the base 301. The cylinder 304 further comprises a radial ring attached to its midsection. The cylinder 304's far end is male threaded. This embodiment further comprises a hollow cylinder 305 that is female threaded at one end to receive the male threaded end of the cylinder 304. The cylinder 305 further comprises a hanging ring or loop 306 attached to its far end. The embodiment further comprises a spring 307 that is attached to the hanging ring 306 and the bottom of a cap 310. The embodiment further comprises a hollow cylinder 308 that encloses the spring 307. The hollow cylinder 308 further comprises a chin rest 309. These features are further depicted and disclosed in details in FIG. 5 and FIG. 6.

Figure 5:
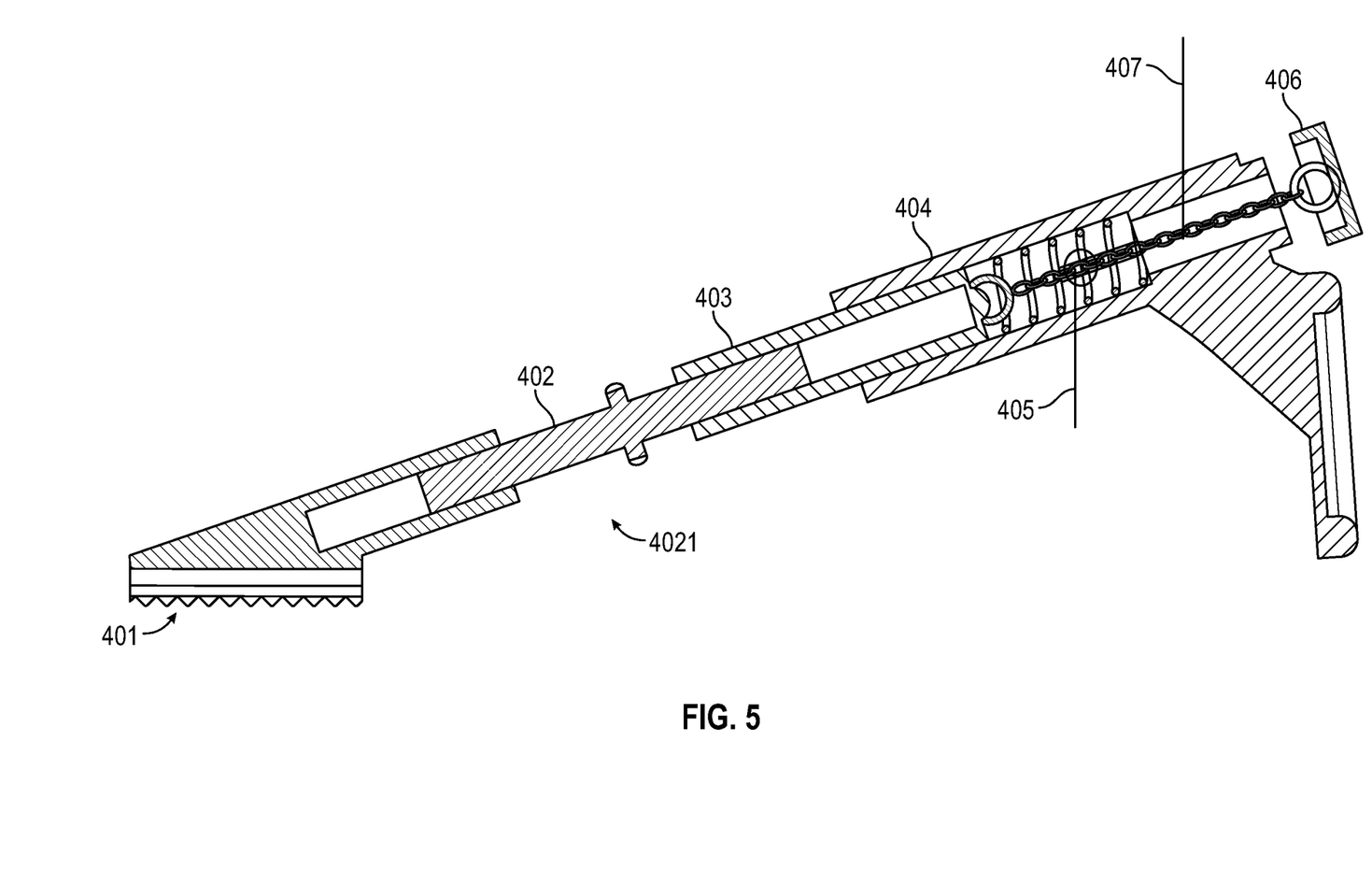
FIG. 5 is a cutaway side-view illustration of the assembled assembly of the support arm mechanism.
Figure 6:
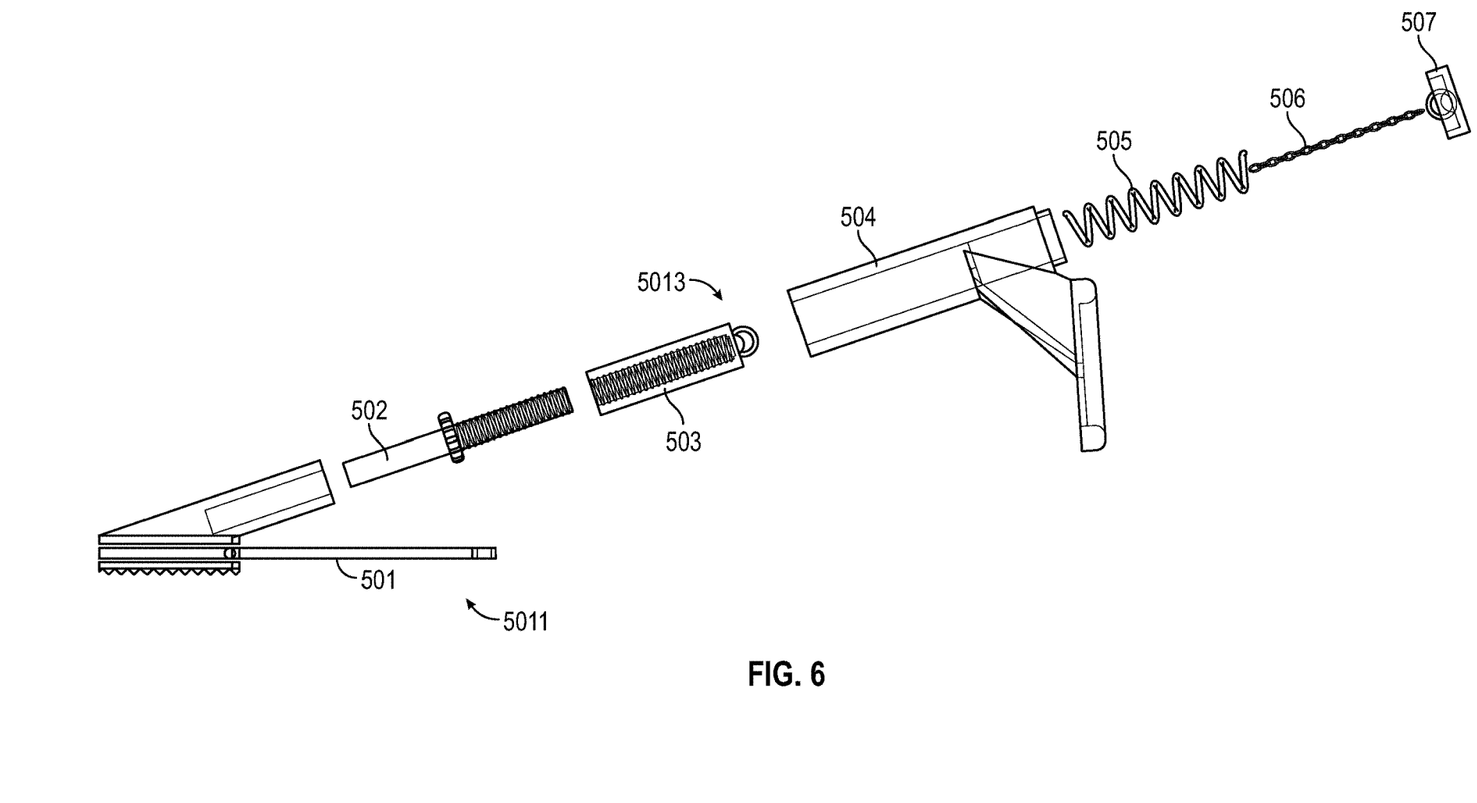
FIG. 6 is a cutaway side-view illustration of an exploded view of the invention.

Reference is now made to FIG. 5 wherein a pictorial illustration shows a sectional view of an assembled embodiment of the current invention. FIG. 6 shows the dependencies and how the various cylindrical components nest and connect to one another.

When in use, the main base 401 of the embodiment rests against the user's sternum. A cylinder 402 is inserted into base 401's bracket. About the midsection of this cylinder 402, it further comprises an extruded radial ring 4021 which serves to ensure that the base 401 and this cylinder 402 are attached at a static height. This radial ring 4021 serves to act as a rotational dial, which a practitioner or user turns in order to raise or lower the support arm. This is accomplished by the previously described threading, cylinder 402 having male threading from the dial to the top of the cylinder which then pairs with the female threading on the lower end of cylinder 403 which receives cylinder 402.

Cylinder 403 is then inserted into component 404 which comprises a hollow cylinder and a chin rest component molded to the outer side of the hollow cylinder. As seen in FIG. 5, the spring 405 rests on the top of the cylinder 403 and is then contained by a hollow cylinder 404, with the cylinder 404 acting as the sides and top. The cylinder 404 also acts a stopper of the spring 405. To achieve this effect, the far end of cylinder 404 has a narrower diameter that is smaller than that of spring 405 and cylinder 404's near end. As such, vertical pressure may be applied to the chin rest component, the far end of component 404, in turn, presses down on the spring 405 and compresses it, raising and lowering component 404 with it.

As can be seen, one end of a chain 407 connects to a hanging ring or loop that is attached to the end of cylinder 403. The other end of the chain 407 threads up and through the top opening of cylinder 404 and is attached to an cap 406. This cap 406 is what allows a practitioner or user to then turn and mechanically lock in the height of this portion of the device, holding the spring in place.

In FIG. 6, an exploded sectional view of an embodiment of the current invention is depicted. This embodiment comprises a base 501 that further comprises attachment arms 5011 that, when in use, wraps the user's chest, locks, and attaches the device to the user's body. The embodiment further comprises a cylinder 502 that has a radial ring attached about the midsection of the cylinder 502. The cylinder 502's far end is male threaded, and screwed into a hollow cylinder 503 that is female threaded. This method of attachment enables the height adjustment feature of the device. The cylinder 503 further comprises a hanging loop or ring 5013 that is attached to its far end. The embodiment further comprises a component 504 that in turn comprises a hollow cylinder and a chin rest component molded to the outer side of the cylinder. The cylinder 503 disposes within the hollow cylinder of the component 504. The embodiment further comprises a spring 505 is also disposed within the hollow cylinder of the component 504. The 504 hollow cylinder has open ends, and the far end opening has a smaller diameter than the diameter of the spring 505. Thus, the spring 505 is contained inside the 504 hollow cylinder, and pushes against the 504 hollow cylinder from the inside. To restrain the spring 505 and prevent the spring 505 from pushing the component 504 away from the assembly, the embodiment further comprises a chain 506 and end cap 507. One end of the chain 506 is attached to the hanging ring 5013, and the other end is attached to the cavity of the end cap 507. The end cap 507 covers the far end opening of the hollow cylinder 504, and the chain 506 and the end cap restrain the component 504, and prevent it from being pushed away by the spring 505. The length or height of this embodiment is adjustable by turning the radial ring on cylinder 502 or the end cap 507, and, consequently, pushing up or pulling down the cylinder 503, and thus extending or contracting the device.

The invention claimed is:

1. A chin and/or neck support device comprising:
an extended-half-round shape, soft base;
said base comprises attachment arms;
said base comprises a bracket that comprises a protruding upward hollow cylinder;
a first cylinder whose near end is disposed within said protruding upward hollow cylinder; and whose far end is male threaded;
a radial ring that is attached to the outer side of said first cylinder about a midsection thereof;
a hollow second cylinder whose near end is female threaded, and far end has a hanging ring attached;
wherein said far end of said first cylinder is screwed into said second cylinder's near end;
a chin support component that comprises a hollow third cylinder, a chin rest component, and an end cap;
wherein the far end of said second cylinder is disposed within said third cylinder;
a spring that is disposed within said third cylinder, and sandwiched between a cavity of said third cylinder and said second cylinder's far end;
a chain that threads through the center of said spring, and whose near end is attached to said hanging ring and whose far end is attached to a bottom of said end cap;
wherein an opening at the far end of said third cylinder has a smaller diameter than said spring.

2. The support device in claim 1, wherein turning said radial ring extends or contracts said support device.

3. The support device in claim 1, wherein said radial ring has a larger diameter than said second cylinder.

4. The support device in claim 1, wherein said end cap is female threaded.

5. The support device in claim 1, wherein said third cylinder is male threaded.

6. The support device in claim 1, wherein said third cylinder is screwed into said end cap.

7. The support device in claim 1, wherein said chin rest component is molded to an outer side of said third cylinder.

8. The support device in claim 1, wherein said chin rest component is attached to an outer side of said third cylinder.

* * * * *